(12) United States Patent
Ford et al.

(10) Patent No.: US 8,283,119 B2
(45) Date of Patent: Oct. 9, 2012

(54) METHODS FOR DETERMINING PROGNOSES AND THERAPEUTIC INTERVENTIONS FOR OVARIAN CARCINOMAS

(75) Inventors: Heide Ford, Denver, CO (US); Kian Behbakht, Greenwood Village, CO (US); Andrew Thorburn, Denver, CO (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 463 days.

(21) Appl. No.: 12/518,315

(22) PCT Filed: Dec. 11, 2007

(86) PCT No.: PCT/US2007/025402
§ 371 (c)(1),
(2), (4) Date: Nov. 12, 2009

(87) PCT Pub. No.: WO2008/073457
PCT Pub. Date: Jun. 19, 2008

(65) Prior Publication Data
US 2010/0099095 A1    Apr. 22, 2010

Related U.S. Application Data

(60) Provisional application No. 60/869,391, filed on Dec. 11, 2006.

(51) Int. Cl.
*C12Q 1/68*    (2006.01)
(52) U.S. Cl. .................. 435/6.11; 435/6.14; 435/7.23
(58) Field of Classification Search .............. 435/6.11, 435/6.14, 7.23
See application file for complete search history.

(56) References Cited

FOREIGN PATENT DOCUMENTS
WO    9949084    9/1999

OTHER PUBLICATIONS

Imam et al. Oncogene 29:4971-4979 (2010).*
Lane, D., et al., "Differential induction of apoptosis by tumor necrosis factor-related apoptosis-inducing ligand in human ovarian carcinoma cells", Gynecologic Oncology, May 10, 2004.
Qamar, Lubna, et al., "Homeobox gene SIX1 and cellular retinoic acid binding protein-II (CRABP-II) are coordinately and differentially expressed in ovarian cancer compared to normal ovary", AACR Meeting Abstracts Online, Abstract #4455, vol. 45, 2004.
Liu, P., et al., "Synergistic antitumor effect of tumor necrosis factor-related apoptosis-inducing ligand combined with cisplatin in ovarian carcinoma cell lines in vitro and in vivo", Int J. Gynecol Cancer, vol. 16, Apr. 2006.
Behbakht, Kian, et al., "Six1 Overexpression in Ovarian Carcinoma Causes Resistance to TRAIL-Mediated Apoptosis and is Associated with Poor Survival", Cancer Research, vol. 67, No. 7, Apr. 1, 2007.
Thorburn, Andrew, et al., "TRAIL Receptor-Targeted Therapeutics: Resistance Mechanisms and Strategies to Avoid Them", Science Direct, Feb. 11, 2008.
Supplementary European Search Report for European Patent Application No. 07862809.6 dated Mar. 11, 2010.
First Examination Report for European Patent Application No. 07862809.6 dated Mar. 31, 2010.

* cited by examiner

*Primary Examiner* — Lynn Bristol
(74) *Attorney, Agent, or Firm* — Snell & Wilmer L.L.P.

(57) ABSTRACT

Methods for determining the prognosis and therapeutic interventions for cancer and for utilizing the expression of the homeoprotein Six1 to determine the prognosis and therapeutic interventions for cancer, in particular for ovarian carcinomas.

11 Claims, 13 Drawing Sheets

| | SEQUENCE | SEQ ID NO. |
|---|---|---|
| 1 GGTAGCAGCA TCCACCGGCA CAAGGCGGTG GGGAGGTTCGG AGGCAGCAAG GCCTTAAAGG CTACTGAGTG | SEQ ID NO. 1 |
| 61 CGCCGGCCGT TCCGTGTCCA CCACCAGTTC TCGGGAGAG GAACCTTCCC TACTCCTCCC CTTGCCGCCC | |
| 121 CACCGCCAAG TTCCGACTCC CGTGGAGGCC GGTTTTCGCC TTTGCAAAGC CTAAGGAGGA GGTTAGGAAC | |
| 181 AGCCGGCGCC CCTCCCCGC CCGAAAATTA GGCGCGGCC CCTGCCTCT CGGCTCCTGCT CCCTGCCGGG | |
| 241 TGCGGCTGGG CGGTGCTGGC CCGTCCCTGC CCAGGGTGCC ATGTCCATGC TTCCGTTCT GCTTTTGGCT | |
| 301 TTACGCAGGA GCAAGTGCG ACTGCTTCAA AGGGGTGTCC TGCAGGCGC AGTTCTGCA GCAAGGCGGA AACCTGGAGC | |
| 361 GCCTGGGCAG GTTCCTGTGG TCACTGCCCG CGGACCA CCTGCACAA AACGAGAGCG | |
| 421 TACTCAAGGC CAAGGCGGTG GTCGCCTTCC ACCGCGGCAA CTTCCGTGAG CTCTACAAGA | |
| 481 TCCTGGAGAG CCACCAGTTC TCGCCTCACA ACCACCCAA ACTGCAGCAA CTGTGGCTGA | |
| 541 AGGCGCATTA CGTGGAGGCC GAGAAGCTGC GGGGCCGCCGC CCTGGGCGCT GTGGGCAAAT | |
| 601 ATCGGGTGCC CCGAAAATTT CCAACTGCGC GCACCATCTG GGACGGCGAG GAGACCAGCT | |
| 661 ACTGCTTCAA AGGGGTGTCC CTGCAGGTCC TGCGCGGAGTG GTACGCCAC AATCCTACC | |
| 721 CATCCCGCG CGAGAAGCGG GAGCCCACCG AGGGCCACCG CTCTACCACC ACCCAGGTCA | |
| 781 GCAACTGGTT TAAGAACCGG CAGCAAACCG ACCGGGACCGG GGAGGCCCAG GAAGGGAGA | |
| 841 ACACCCAAAA CAATAACTCC TCCTCCAACA AGAGAAGT CTCCAAAAGT CTGGAAGGG | |
| 901 ACTCGGTCCT CATGTCCAGC GGCAATATGG AATTCTCACC TCCCAAGT CTGAAGGGA | |
| 951 ACTGTCCCTT TCTGTCCAG GCCACGCCAG GCCACAAC TATCTCCTCC | |
| 1021 CGGCTTAAC AGCCTCGCT CCGCCCCCTC ACTCCCAGAC TGGTGGACTT CAGCCAGAC | |
| 1081 ACTCCGCT CGAAGGGCC CTGGAGCAG CAACCAACTGC AGGGACTAGG GTGGGGAGGG | |
| 1141 ACTGGGCCT AGGCCCTGCA TGGAAAATT AGGACCACCT CAAGCAAAT GACACTTGTA | |
| 1201 AATAGAAATC ACAAATATCT TTTAAAAAT CAAAACCAAC AGCGATCTCA TAAAGGAATG | |
| 1261 GTGGACTTC CCAACTCTTA CCACTTTGC ATTTTCCTTC CCAATGCAGA AGCTTAATCT | |
| 1321 CCTCTTTCT CCACTTTTT | |

| 1 MSMLPSFGFT QRQVACVCEV LQQGGNLERL GRFLMWSLPAC DHLHKNESVL KAKAVVAFHR | NO. 2 |
| 61 GNFRELYKIL ESHQFSPHNH PKLQQLWLKA HYVRAEKLRG RPLGAVGKYR VRHKFPLPRT | |
| 121 IWDGEFTISYC FKEKSRGVLR EWYAHNPYPS PREKRBLAEA TGLTTTQVSN WFKNRRQRDR | |
| 181 AAEAKERNT EINNNSSSNKQ NQLSPLEGGK PLMSSEEHF SPQSPDQNS VLLQGNMGH | |
| 241 ARSSNYSLPG LFASQPSHGL QTHQHLQDS LLGPLTSSLV DLGS | |

FIG. 1

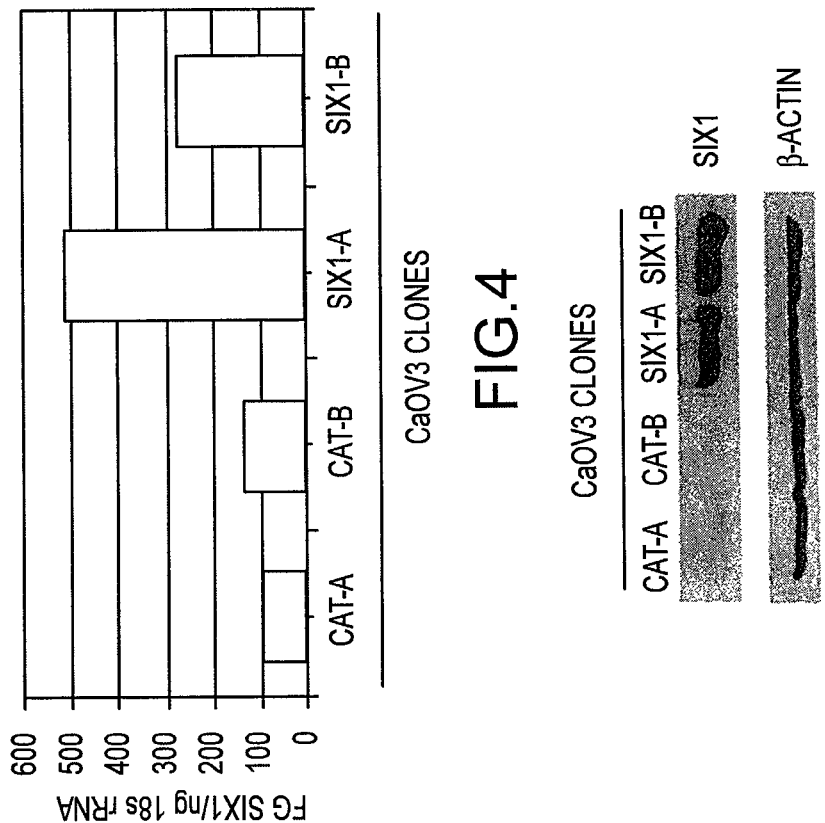
FIG. 4
FIG. 5
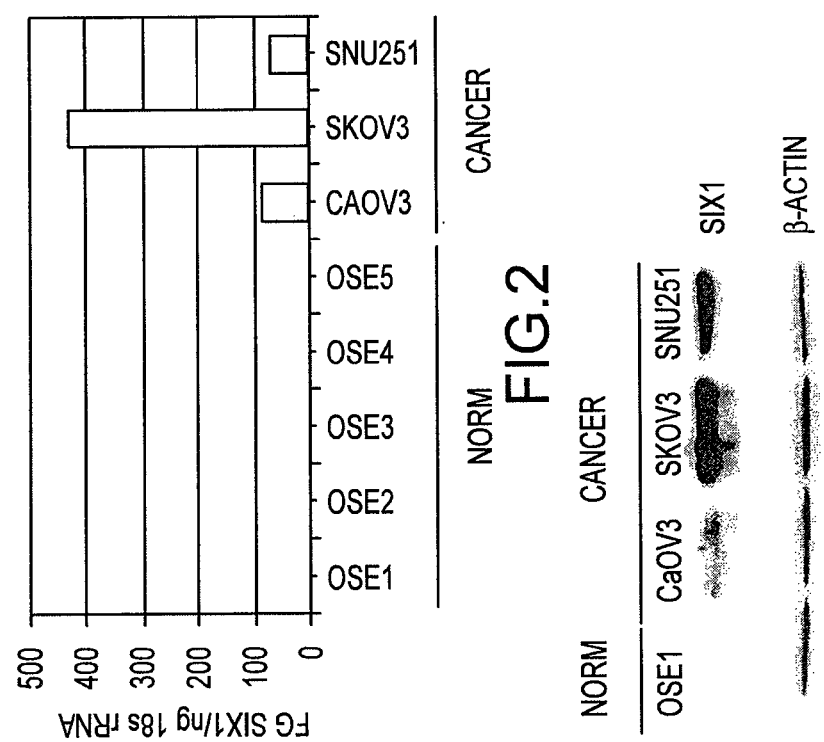
FIG. 2
FIG. 3

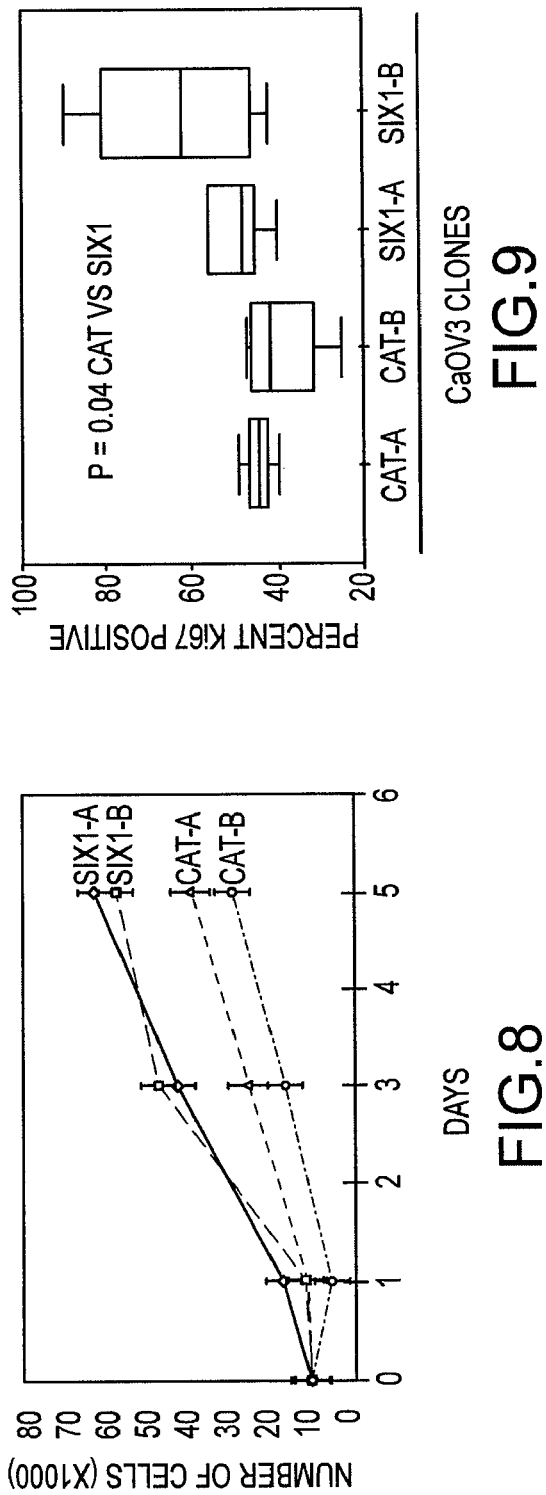
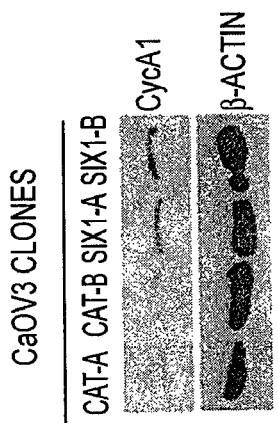
FIG. 9
FIG. 8
FIG. 10

| CONSTRUCT | TARGETED SEQUENCE | SEQ ID NO. |
|---|---|---|
| SIX1C (TARGETS REGION IN SIX1 mRNA) | GAA CGA GAG CGU ACU CAA G | NO. 3 |
| SIX1F (TARGETS REGION IN SIX1 mRNA) | AGU CCA GAC CAG AAC UCG G | NO. 4 |
| LUC (TARGETS REGION IN LUCIFERASE mRNA) | CGU ACG CGG AAU ACU UCG A | NO. 5 |

FIG. 19

| PRIMER/PROBE | SEQUENCE (5' TO 3') | SEQ ID NO. |
|---|---|---|
| SENSE | CAC CTC CCC AAA GTC CAG AC | NO. 6 |
| ANTISENSE | CCT GGC GTC GCC CAT A | NO. 7 |
| PROBE | CGG TCC TTC TGC TGC AGG CA T | NO. 8 |

METHODS FOR DETERMINING PROGNOSES AND THERAPEUTIC INTERVENTIONS FOR OVARIAN CARCINOMAS

CROSS-REFERENCE TO RELATED APPLICATIONS

This application is U.S. national phase filing under 35 U.S.C. §371 of PCT/US2007/025402 filed Dec. 11, 2007 and claims priority from U.S. Provisional Application No. 60/869,391 which was filed on Dec. 11, 2006.

GOVERNMENT RIGHTS

This invention was made with government support under grant number RO1 CA095277 and K12 CA086913 awarded by the National Institutes of Health. The government has certain rights in the invention.

SUBMISSION OF SEQUENCE LISTING

Applicants hereby submit simultaneously and incorporate by reference herein the sequence listing identified as 516060116.TXT, created on Apr. 16, 2008, with a file size of 6 KB, pursuant to 37 C.F.R. §1.52(e)(5).

FIELD OF INVENTION

The invention is generally directed to determining the prognosis and therapeutic interventions for ovarian carcinomas and, more particularly, to utilizing the expression of the homeoprotein Six1 to determine the prognosis and therapeutic interventions for ovarian carcinomas. The present invention is also directed to utilizing the expression of the homeoprotein Six1 to determine therapeutic interventions for other cancers.

BACKGROUND OF THE INVENTION

Ovarian carcinoma is the deadliest gynecologic malignancy and one of the leading causes of cancer deaths for females. Because ovarian cancer is often diagnosed only after the disease has reached an advanced stage, the majority of patients require additional treatment after surgical removal of the tumor and many of those patients still die from the disease. Although greater than 70% of patients with advanced ovarian cancer respond to primary chemotherapy, most ultimately develop resistance, leading to an overall 5-year survival below 20%. For this reason novel approaches are being sought to overcome chemoresistance and to develop more effective therapies.

Currently, biological therapies are being considered as the next approach in the fight against ovarian cancer. These therapies have the potential to selectively target tumors, to minimize toxicity, and to overcome the resistance often observed with conventional therapies. One such therapy involves activating the Tumor Necrosis Factor-Related Apoptosis-Inducing Ligand (TRAIL)-pathway, that selectively induces apoptosis in tumor cells while sparing normal cells. Specifically, TRAIL triggers apoptosis rapidly through the extrinsic apoptotic pathway mediated by the death receptors, DR4 and DR5, on the cell membrane. Upon TRAIL ligand-mediated activation of the death receptor, its intracellular death domain attracts the Fas-associated death domain (FADD) adaptor molecule, which further recruits the initiator caspases 8 and 10 to the death receptor to form the death-inducing signal complex (DISC). This process ultimately results in the activation of the terminal executioner caspases 3, 6, and 7, thereby leading to cell death. Importantly, cell culture and mouse xenograft experiments have demonstrated that TRAIL can exert selective cytotoxic activity against ovarian carcinoma cells with limited effects to normal cells.

TRAIL has been implicated in several aspects of tumorigenesis including innate immune-surveillance against tumors, inhibition of tumor initiation and metastases, and in the response to conventional chemotherapy. For example, TRAIL-deficient mice show increased tumor susceptibility in response to the chemical carcinogen methylchloanthrene, and increased experimental and spontaneous metastasis. In addition, mutations in TRAIL receptors have been linked to metastatic breast cancer. Thus, activating the TRAIL pathway clinically could induce cell death and prevent metastatic disease, and those tumors that devise mechanisms to escape TRAIL-mediated apoptosis might be more metastatic.

These observations provide the basis for development of TRAIL pathway agonists (TRAIL and TRAIL receptor agonistic antibodies) for clinical trials currently in progress. However, such trials are impeded by our lack of knowledge regarding the underlying basis of tumor susceptibility to TRAIL pathway-induced death. Accordingly, there is a continued need to identify the determinants of TRAIL pathway sensitivity in ovarian tumors, and other cancers, in order to improve our ability to use the TRAIL pathway agonists that are in clinical development alone and in combination with chemotherapy.

SUMMARY OF THE INVENTION

The invention is directed to utilizing the expression of the homeoprotein Six1 to determine therapeutic interventions for cancers. The invention is also particularly directed to methods for determining the prognosis and therapeutic interventions for ovarian carcinomas and to utilizing the expression of the homeoprotein Six1 to determine the prognosis and therapeutic interventions for ovarian carcinomas.

The present invention is based, at least in part, on the demonstration that homeoprotein Six1 expression is related to the tumorigenicity of ovarian carcinoma and that it not only increases ovarian carcinoma cell proliferation, but that it also protects ovarian carcinoma cells from TRAIL-mediated apoptosis. Moreover, since Six1 over-expression has been observed in numerous cancers including, but not limited to, breast cancer, rhabdomyosarcoma, hepatocellular carcinoma, and Wilms' tumors, the use of TRAIL reagents in therapy for these and other cancers may prove ineffective without targeting Six1 expression.

One exemplary embodiment of the present invention includes a method for determining therapeutic intervention for cancer which includes the steps of obtaining a biological sample from a subject having cancer, determining whether the biological sample possesses an over-expression of Six1, and selecting a TRAIL agent for therapy when Six1 is not overexpressed. The biological sample may be a tumor sample, including an ovarian tumor sample.

Another exemplary embodiment of the present invention includes a method for determining therapeutic intervention for ovarian carcinoma which includes the steps of obtaining an ovarian tumor sample from a subject, determining an amount of at least one of Six1 protein and Six1 mRNA in the ovarian tumor sample, determining whether the amount of Six1 protein or Six1 mRNA is over-expressed in the ovarian tumor sample compared to a control, and selecting a TRAIL agent for therapy when Six1 is not over-expressed. Alternatively, instead of selecting a TRAIL agent for therapy, the method for determining therapeutic intervention for ovarian carcinoma may include the step of selecting a therapy that does not include TRAIL when Six1 is over-expressed.

The present invention also includes a method for determining the prognosis of a subject with ovarian carcinoma which includes the steps of obtaining an ovarian tumor sample from a subject, determining the amount of Six1 protein or Six1 RNA expressed in the ovarian tumor sample, and forming a prognosis based on the amount of Six1 protein or Six1 RNA. The prognosis may be made by comparing the amount of Six1 protein or Six1 RNA expressed in the ovarian tumor sample to a control and making a prognosis of increased mortality when Six1 expression levels in the ovarian tumor are greater than 300 fg/ng rRNA.

Still another exemplary embodiment of the present invention includes a method for determining therapeutic intervention for cancer which includes the steps of obtaining a biological sample from a subject having cancer, determining whether the biological sample possesses an over-expression of a protein that resists TRAIL, and selecting a non-TRAIL agent for therapy that is not cross-resistant to chemotherapy when the biological sample does possess an over-expression of a protein that resists TRAIL. The protein may be the homeoprotein Six1 and the biological sample may be a tumor sample, including an ovarian tumor sample.

BRIEF DESCRIPTION OF THE DRAWINGS

FIG. 1 is the complete cDNA sequence and deduced amino acid sequence of human SIX1.

FIGS. 2-7 show that Six1 is overexpressed in ovarian carcinoma cell lines compared to normal ovarian surface epithelial cells. FIG. 2 shows qRT-PCR for Six1 in three ovarian carcinoma cell lines (OCC) compared to five normal ovarian surface epithelial (OSE) cell lines. FIG. 3 shows Western blots of nuclear extracts from the same cells as in FIG. 2. FIGS. 4 and 7 show overexpression of Six1 mRNA in CaOV3 cells transfected with Six1. qRT-PCR demonstrates 2-5-fold over-expression of Six1 mRNA in CaOV3-Six1 transfectant clones compared to CaOV3-CA T controls. FIG. 5 shows Western blot analysis of whole cell lysates for SIX1 protein in CaOV3-Six1 clones. (Note—no endogenous SIX1 protein can be observed in whole cell lysates from CaOV3 cells although it can be observed in nuclear extracts from the same cell type—FIG. 3). FIG. 6 shows a Northern blot analysis of nuclear extracts from the same cells as in FIG. 2.

FIGS. 8-11 show that Six1 increases OCC proliferation concomitant with Cyclin A1 induction. FIGS. 8 and 11 show cell numbers in CaOV3-Six1 cells and CAT transfected controls. In FIG. 8, higher cell numbers are observed at 3 and 5 days post plating in the CaOV3 cells (p<0.001). Solid black line: Six1-A, dashed line: Six1-B, dotted line: CAT-A, gray line: CAT-B. FIG. 9 shows Ki-67 positive cells in CaOV3-Six1 clones compared to CAT controls. Percent of positive cells in Six1-A and Six1-B combined is 56%±16% compared to CAT-A and CAT-B combined 41%±8%; P=0.04. FIG. 10 shows Western blot analysis of cyclin A1 (CycA1) protein expression in CaOV3-Six1 transfectants and CaOV3-CA T controls.

FIG. 12 shows the percent of cells with condensed nuclei in CaOV3-Six1 clones compared to CaOV3-CAT cells. FIG. 13 shows the effect of 40 h of TRAIL on Six1-overexpressing CaOV3 and CAT control transfectants. Cytotoxicity was measured using the MTS assay.

FIG. 14 shows a representative SIX1 Western blot analysis demonstrating efficiency of knock-down with siRNA constructs; only the Six1 C construct effectively knocks down SIX1 expression. Confirmatory Western blots were performed for each experiment and showed similar results. FIG. 15 shows the effect of TRAIL on cells transfected with a control (Luc, dotted line) construct, an efficient Six1-targeting construct Six1 C (solid black line) and an ineffective (see Western Blot) Six1-targeting construct Six1 F (dashed line).

FIG. 16 shows qRT-PCR for Six1 in normal ovary (n=5), cystadenoma (n=7), early stage (stage I) ovarian carcinomas (n=5) and late stage metastatic (stages II-IV) ovarian carcinomas (n=19). Dotted line runs across graph at 100 fg Six1/ng rRNA. FIG. 17 shows survival curves for patients with tumor Six1 levels>300 fg/ng rRNA (median follow-up 17 months, Log Rank p=0.02).

FIG. 19 is a table listing mRNA sequences targeted by pSUPER sRNA vectors.

DETAILED DESCRIPTION

Figure 6:
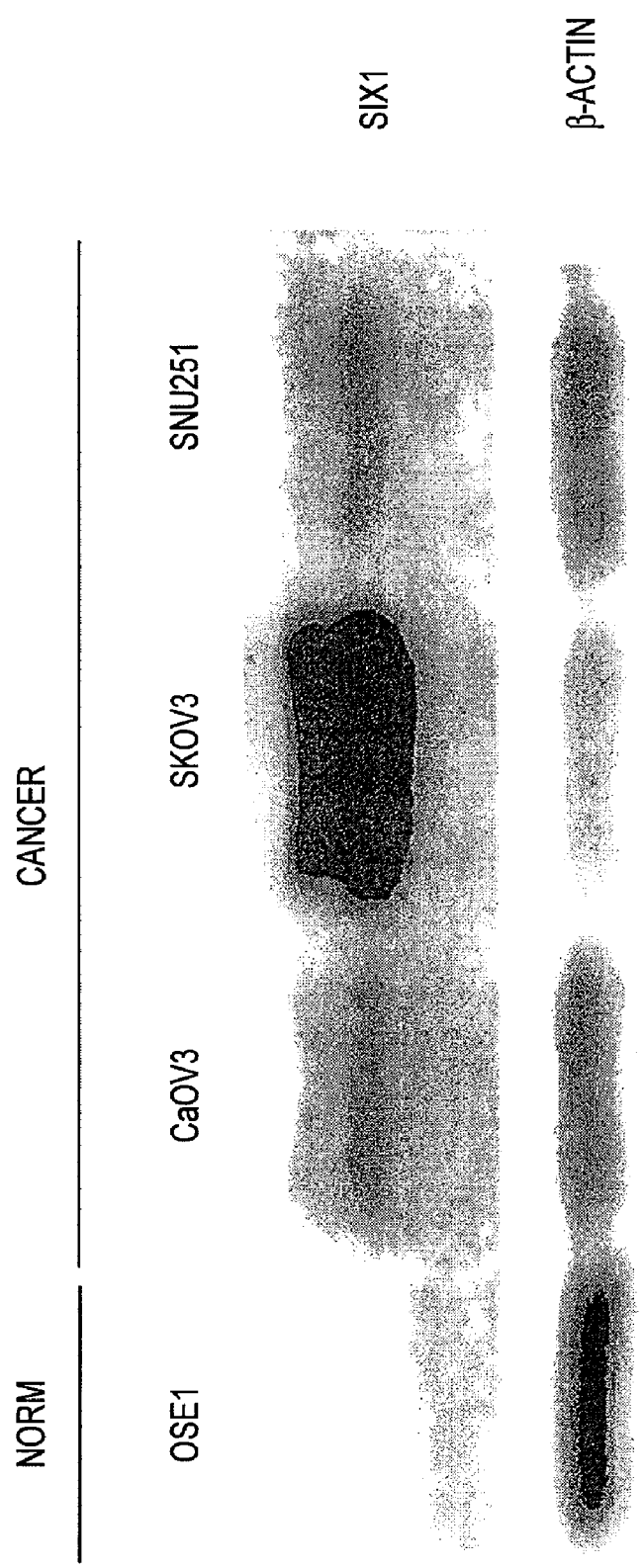

Tumorigenesis can arise from inappropriate activation of developmental genes in mature tissues. The invention is based, at least in part, on the discovery that the developmental regulator Six1 is overexpressed in ovarian carcinoma cell lines (OCC) compared to normal ovarian surface epithelium (OSE), and that its expression correlates with a more malignant phenotype. As observed in other cancers, Six1 overexpression in OCC leads to increased A-type cyclin expression and increased proliferation. The invention is also based, at least in part, on the discovery that Six1 overexpression renders OCC resistant to TNF-related apoptosis inducing ligand (TRAIL)-mediated apoptosis, but not Fasl-mediated apoptosis, and Six1 knockdown in the aggressive and TRAIL-resistant SKOV3 ovarian carcinoma line dramatically sensitizes the cells to TRAIL. Because inactivation of the TRAIL response has been linked to metastasis, and because activation of the TRAIL apoptotic pathway is currently in clinical trials against ovarian carcinoma, normal ovarian and carcinoma specimens were screened for Six1 mRNA. Six1 was overexpressed in 60% of the early and 68% of the advanced stage ovarian carcinomas examined, with metastatic carcinomas expressing 3-fold higher Six1 mRNA levels compared to early stage (non-metastatic) tumors. Importantly, in patients with metastatic disease, high Six1 expression was associated with significantly shortened survival (p=0.02).

The present invention is directed to the finding that the developmental regulator homeoprotein Six1 is a modulator of the TRAIL pathway. Six1 is expressed during embryogenesis but lost in most differentiated tissues and has been implicated in the etiology of numerous cancers including breast cancer, rhabdomyosarcoma, hepatocellular carcinoma, and Wilms' tumors. During normal development Six1 stimulates the proliferation and survival of progenitor cells, and when expressed out of context, Six1 can aberrantly promote proliferation, contributing to tumorigenesis. The present invention is directed to the discovery that Six1 expression is related to the tumorigenicity of ovarian carcinoma, and that it not only increases ovarian carcinoma cell proliferation, but that it also protects ovarian carcinoma cells from TRAIL-mediated apoptosis. This discovery has important implications for the use of TRAIL reagents in ovarian cancer therapy and other cancer therapies.

Methods

Cell lines and cell culture. The OCC lines CaOV3 and SKOV3 were obtained from ATCC (Rockville, Md.). The cell line SNU251 (44) was provided by Dr. Jeff Holt. Cell lines were maintained in DMEM (CaOV3) or McCoy's 5-α (SKOV3) or RPMI-1640+1% Insulin-Transferrin-Selenium A (SNU251), all with 10% FBS at 3JDC and 5% CO2. OSE were harvested from patients undergoing oophorectomy. Epithelial origin was verified by pan-cytokeratin staining.

Transfection for Six1 overexpression and knockdown. Full length Six1 cDNA [SIXFL, (22)] or control pcDNA3.1 (CAT) plasmids were transfected into $1 \times 10^6$ CaOV3 or SNU251 cells using Superfect according to manufacturer specifications (Qiagen, Valencia, Calif.). Transfectants were selected with 400 µg/ml G418. Approximately 2 weeks later, individual clones were isolated and propagated. Six1 expression was verified by qRT-PCR, Northern, and Western blots.

Transient transfections for short interfering RNA (siRNA) experiments were performed by resuspending SKOV3 cells at $3 \times 10^6$ cells/ml of electroporation buffer (2 mM Hepes pH 7.2, 15 mM $K_2HPO_4/KH_2PO_4$ pH7.2, 250 mM mannitol, 1 mM $MgCl_2$). 800 µl of cell solution was added to 16 µg DNA—either pSUPER Six1C, pSUPER Six1F, or pSUPER luciferase (for description of constructs see FIG. 19). Cells were then electroporated in 4 mm gap electroporation cuvettes at 250V, 2 ms duration, 1.5 s intervals, 15 times, and transferred to plates with warmed DMEM+10% FBS. Knockdown of Six1 was confirmed by Western blotting of nuclear extracts both at the time of plating for the TRAIL assay (see below), and at the time of completion of the TRAIL assay. Functionality of the pSUPER Luciferase construct was tested by co-transfection with a cyclin D1-promoter luciferase expressing construct (CD1-Luc, a kind gift from Justin Lamb and Mark Ewen), followed by analysis of luciferase activity.

Quantitative real time RT-PCR (qRT-PCR) and Northern Blot analysis. Total RNA was extracted from cultured cell lines or patient specimens stored in RNA later using standard TRIzol extraction (InVitrogen Life Technologies). Purity, concentration and integrity of total RNA was verified using a spectrophotometer as well as the RNA 6000 Nano assay (Agilent technologies, Palo-Alto, Calif.) and visualization of the 18 s and 28 s rRNA bands. Northern blot analysis was performed as previously described using 15 µg of high quality RNA per sample and standardized with l3-actin and Ethidium Bromide (EtBr) staining. For qRT-PCR, 1 µg of extracted RNA was analyzed by rRNA amplification to verify integrity of the RNA. High quality specimens were then analyzed for Six1 mRNA levels using the ABI Prism$^R$ 7700 sequence detection system (Applied Biosystems, Foster City, Calif.) and Six1 specific primers and taqman probes (Primers and probes are listed in FIG. 21). Six1 cDNA and control rRNA standard curves were generated with each experiment. Results are reported as fg Six1/ng 18S rRNA. Experiments were repeated in triplicate and representative experiments are shown.

Protein isolation and Western blots. For whole cell lysates, samples were lysed on ice in RIPA buffer. Nuclear extracts were performed by the Dignam method. Protein concentration was determined by the Lowry method. 30 µg of each protein sample was loaded on a 12% SDS polyacrylamide gel and transferred to PVDF. Membranes were probed with antibodies to Six1 and to Cyclin A 1 (BD Biosciences), and were normalized to l3-actin (Sigma-Aldrich Corporation).

Proliferation Assays. 10,000 cells/well in 6-well plates were seeded. Cells were counted with trypan blue dye exclusion at days 1, 3 and 5. Counts were reported as means of 3-6 wells. Each cell growth assay was repeated at least once, at least in triplicate. For assessment of the percent of cells in the cell cycle using Ki67 staining (Dako Corporation), immunocytochemistry was performed on 5-8 µm sections of formalin-fixed paraffin embedded cell blocks of cultured cells. Sections were developed using the ABC method (Vector Laboratories) and counterstained with hematoxylin. Three randomly selected 160× fields/slide were analyzed visually by a blinded observer and percentage stained cells were quantified and analyzed.

Analysis of tumor growth in SCID mice: All of the experiments involving animals were approved by the UCDHSC Animal Care and Use Committee. Female 3-4 week old CB-17 strain SCID mice (Taconic) were injected subcutaneously on both flanks with $1 \times 10^7$ SKOV3 or CaOV3 cells/side. Mice were monitored daily. Time to tumor development was recorded and tumors were measured daily after their appearance. Mice were euthanized before tumors reached 2 cm in diameter.

Detection of apoptotic cell death. Cell lines were plated in chambered slides in duplicate in at least two separate experiments. Once the cells reached 70% confluency, they were fixed with 40 g/l PBS buffered 4% formaldehyde for 20 mins after which they were stained with Hoechst 33258 (10 mg/l). Slides were then examined using fluorescence microscopy. Apoptotic cells were defined on the basis of condensed nuclear morphology. Six random fields at 100× magnification were counted per slide by a blinded observer, and the number of apoptotic cells/total nuclei were recorded.

Dose-response curves for TRAIL and Fas-ligand mediated growth inhibition. For CaOV3 and SNU251 transfectants, 5,000 cells were plated in each well of a 96 well plate and treated with varying concentrations of full-length recombinant soluble TRAIL (rhTrail from R&O Biosystems), Fas Ligand (Alexis/Axxora), or Media +OMSO for 40 hours. Cell viability was assessed using the MTS assay (Promega). For SKOV3 cells in which Six1 was knocked-down, 1000 cells/well were plated as above 48 hours after electroporation. The rest of the assay was performed as outlined for CaOV3 and SNU251 cells. Means of six wells are reported and experiments were repeated at least once in sextuplet. Representative dose-response curves are shown.

Patient specimens. Fresh tissue specimens were obtained under an approved IRB protocol immediately after evaluation by a pathologist and stored in RNAlater stablization buffer (Qiagen, Valencia, Calif.). Staging was performed by one of two authors (KB or SD). A portion of each specimen was mounted in OCT compound, snap-frozen and stored at −80° C. and another portion was fixed in formalin and paraffin embedded. 5-8 µm sections were cut and verified using hematoxylin & eosin staining.

Statistical analysis. Results were compared using student's t-test and one way ANOVA for normally distributed variables and X2, Fischer's Exact test and Mann-Whitney-U test for non-parametric variables. Survival data was analyzed using the Kaplan-Meier method with analysis of significance via the Log-rank test. The SPSS(SPSS, Inc., Chicago Ill.) data analysis software was used.

Results and Findings

Six1 is expressed in epithelial ovarian carcinoma cell lines but not ovarian surface epithelial cells. The Six1 homeobox gene is overexpressed in a number of cancers, including breast cancer, rhabdomyosarcomas, hepatocellular carcinoma, and Wilms' tumor. With respect to the present invention, it was found that Six1 is also overexpressed in ovarian carcinoma. The expression of Six1 in a number of ovarian carcinoma cell lines (OCC) and cultured normal ovarian surface epithelial cells (OSE) were examined. Six1 mRNA, as measured by both Northern blot analysis (FIG. 6) and quantitative RT-PCR (qRT-PCR) (FIG. 2), is increased in OCC (CaOV3, SKOV3, and SNU251) compared to OSE. FIG. 3 shows that SIX1 protein expression follows the same pattern with highest levels observed in the SKOV3 cell line.

SKOV3 cells, which express higher levels of Six1 than CaOV3 cells, are reported to be almost 3.5 times as resistant to cisplatin treatment as CaOV3 cells, and are also more resistant to TRAIL-mediated apoptosis, suggesting that they are a more aggressive OCC line. Soft agar assays were performed on three OCC lines (SKOV3, CaOV3, SNU251) to compare their tumorigenic potential. Both CaOV3 and SKOV3 cells grew in soft agar while SNU251 cells did not form colonies in soft agar (not shown). Accordingly, SNU251 cells are the least tumorigenic of the three OCC lines. Ten million cells of each CaOV3 and SKOV3 cell line were injected subcutaneously into SCID mice to assess their tumorigenic potential in vivo. Tumors grew in 4/6 (66%) and 24/24 (100%) of animals injected with CaOV3 and SKOV3 cells respectively, with a mean latency of 7 weeks for CaOV3 cells compared to 4 weeks for SKOV3 cells. These data, taken together with reports demonstrating that SKOV3 cells show increased resistance to both TRAIL-mediated apoptosis and chemotherapeutic agents, demonstrate that increased Six1 expression correlates with increased tumorigenic potential of ovarian carcinoma cells.

Figure 7:
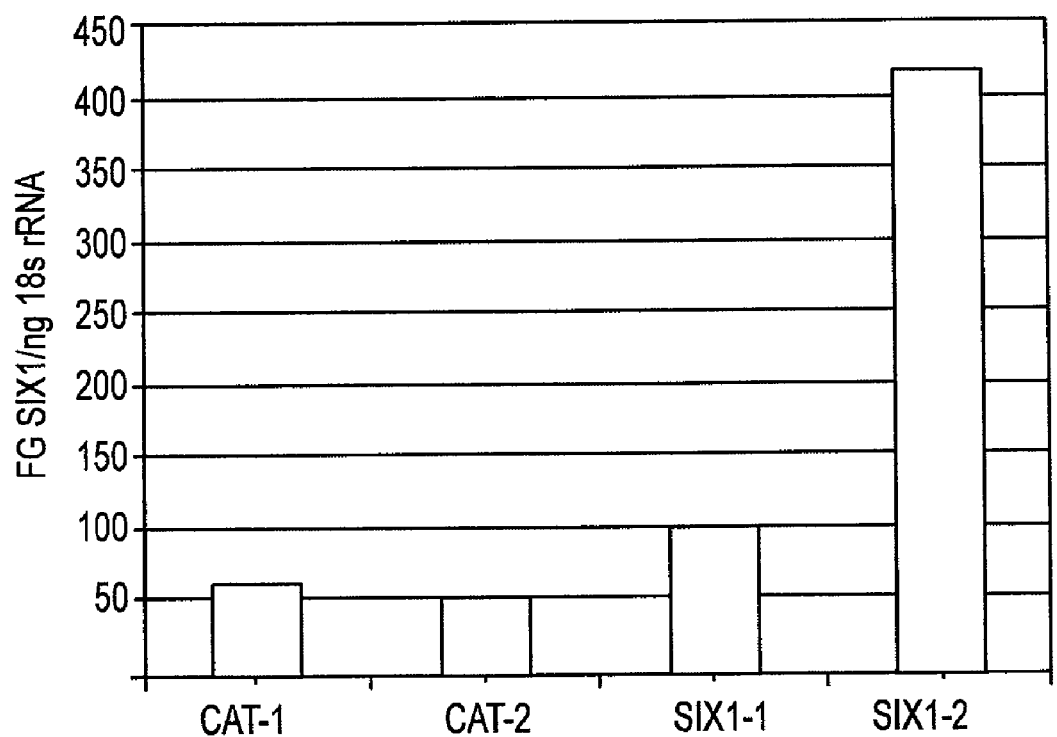

Six1 over-expression promotes a proliferative and anti-apoptotic phenotype in ovarian carcinoma cells. Six1 over-expressed in both CaOV3 and SNU251 cells, both which express Six1 endogenously but at significantly lower levels than the SKOV3 cell line. Stable Six1 and control CAT (chloramphenicol acetyl transferase) transfectants were generated and examined for Six1 mRNA and protein as shown in FIGS. 4, 5 and 7. Two stable Six1-overexpressing clones and two CAT control clones from each line were chosen for further analyses. The levels of overexpression of Six1 (fg/ng rRNA) achieved in the CaOV3 and SNU251 clones was less than or equivalent to the level of expression of endogenous Six1 in SKOV3 cells as determined by qRT-PCR (Average level of expression in SNU 251-Six1 clones=262 fg/ng rRNA, CaOV3-Six1 clones=395 fg/ng rRNA, SKOV3=437 fg/ng rRNA). Therefore, the gene was over-expressed at the physiologic levels expressed in aggressive OCC.

Figure 11:
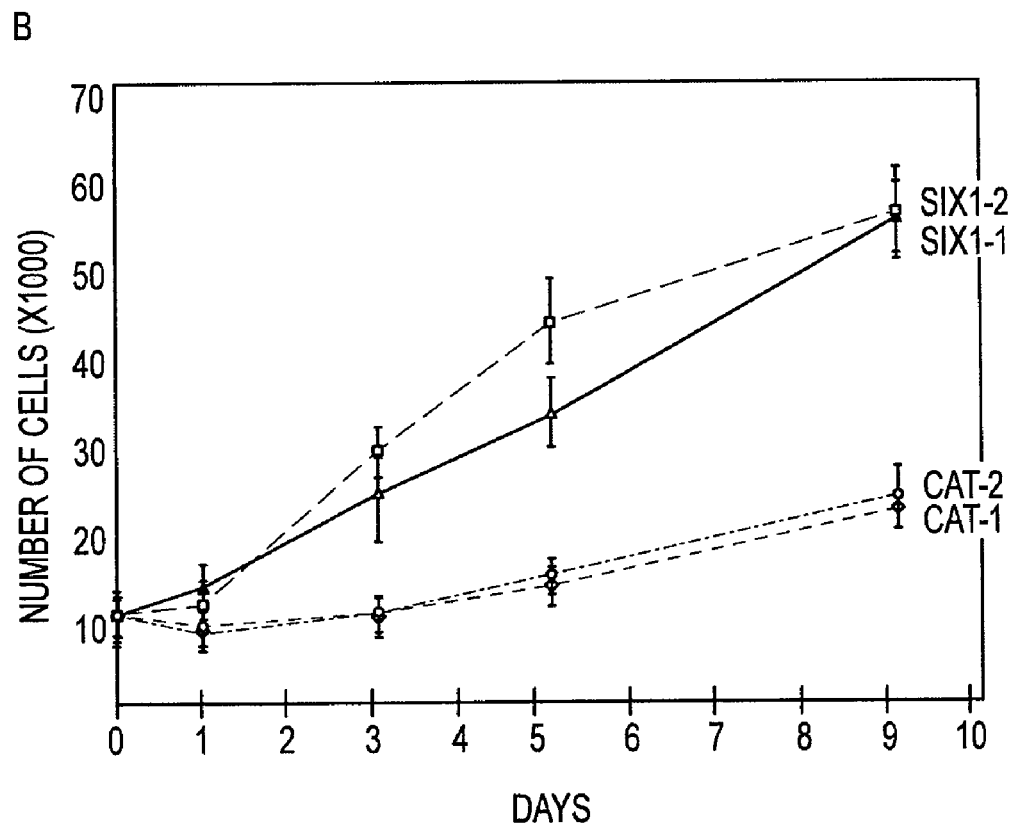

Six1 promotes the proliferation of precursor cells in normal development and contributes to breast cancer and rhabdomyosarcoma cell proliferation. The growth of CaOV3-Six1 and SNU251-Six1 cells was compared to CaOV3-CAT and SNU251-CAT control cells. The Six1-overexpressing cells increased in number at a faster rate than CAT control cells in both cell types (FIGS. 8 and 11). The proliferative index of the CaOV3 transfectants using Ki-67 staining was measured to determine whether Six1 overexpression influences proliferation per se in OCC as opposed to simply decreasing apoptosis. In CaOV3-Six1 clones, 56%±16% of the cells (average of two clones) were positive for Ki-67, compared to 41%±8% of the CaOV3-CAT cells (average of two clones); an increase that is statistically significant (p=0.04) (FIG. 9). Consistent with previous results in breast cancer cells where Six1-dependent increases in proliferation are mediated by cyclin A1, Six1 overexpression in OCC led to an upregulation of cyclin A1 (FIG. 10).

Figure 12:
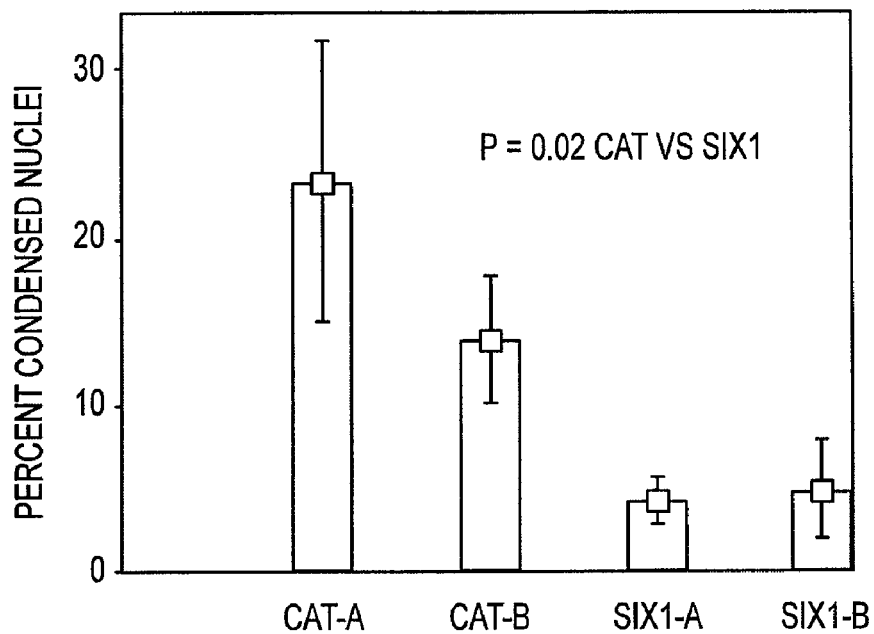
FIGS. 12-13 show that Six1 overexpression leads to a decrease in basal apoptosis and to resistance to TRAIL.

Organs in Six1 knockout mice have shown decreased proliferation as well as increased apoptosis, suggesting that the Six1 protein may confer both proliferative and survival advantages. However, the role of Six1 in cancer cell survival has not been established. Hoechst staining for nuclear chromatin condensation revealed at least a 3-fold decrease in basal apoptosis in Six1-overexpressing cells compared to CAT controls (FIG. 12, p=0.02), suggesting that Six1 overexpression in OCC increases net cell numbers by decreasing apoptosis in addition to stimulating proliferation.

Figure 13:
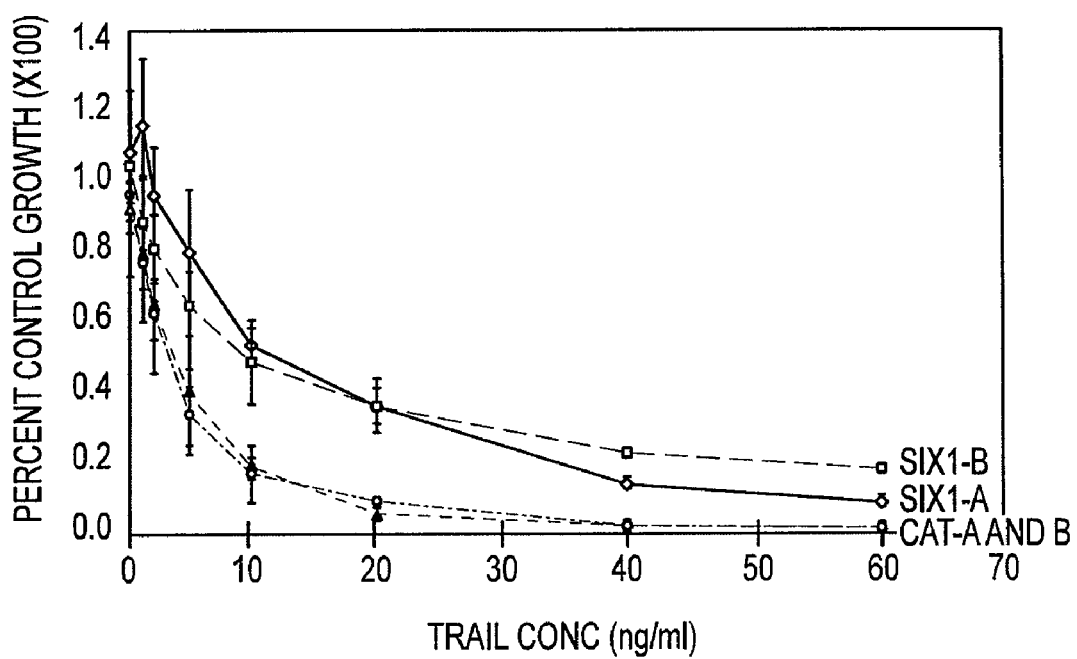
Figure 18:
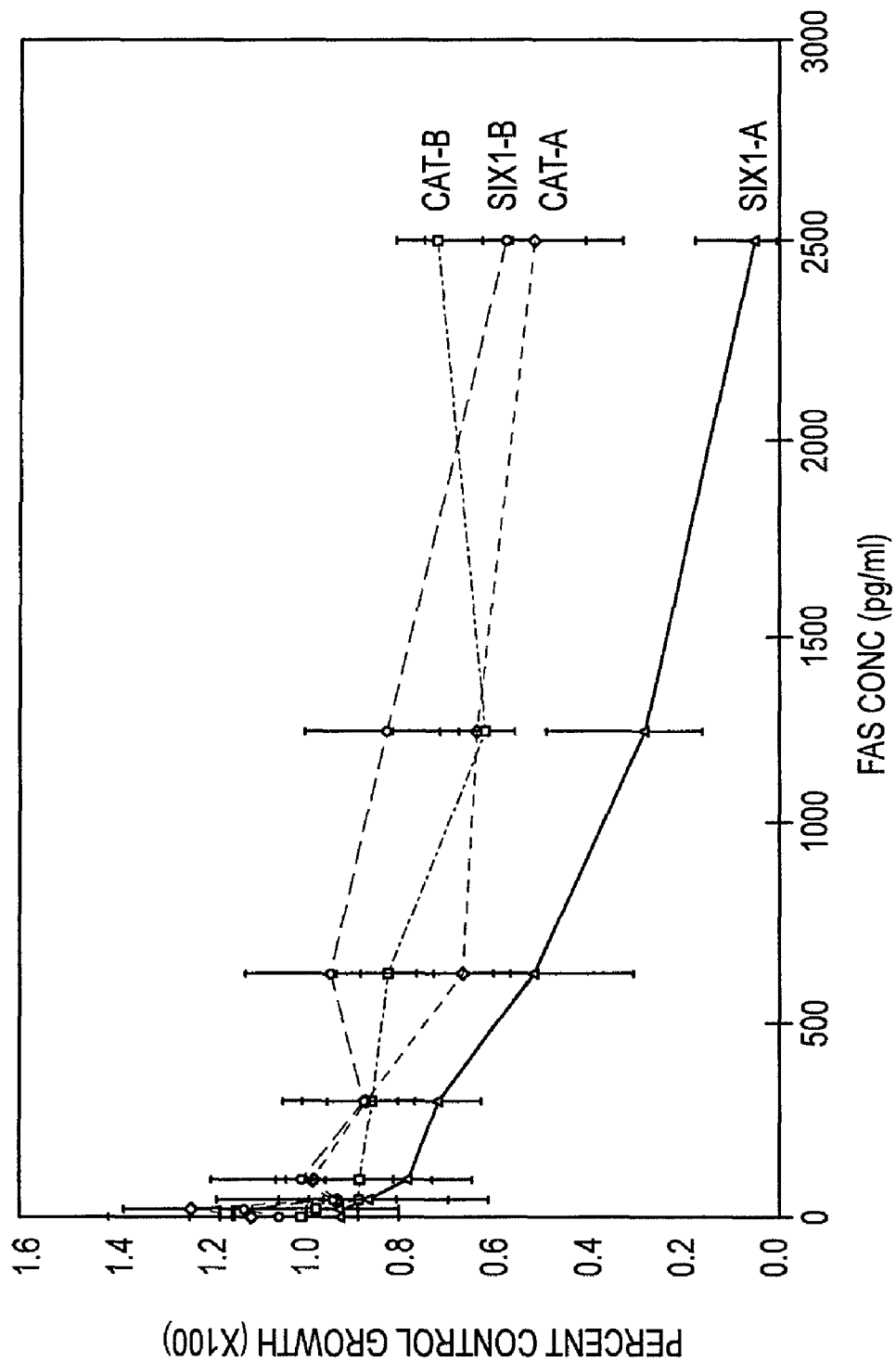
FIG. 18 shows the effect on FasL of Six1 overespression in CaOV3.

TRAIL resistance in cell lines overexpressing Six1. As FIG. 13 shows, Six1 overexpression in CaOV3 cells decreased TRAIL sensitivity from an $IC_{50}$~3 ng/ml TRAIL in CaOV3-CAT clones to an $IC_{50}$~11 ng/ml TRAIL in CaOV3-Six1 clones. Similar results were obtained in SNU251 cells where the $IC_{50}$ was ~7 ng/ml TRAIL in SNU251-CAT clones and ~15 ng/ml in SNU251-Six1. In contrast, Six1 overexpression did not confer resistance to the Fas-ligand (FasL) (FIG. 18).

Figure 14:
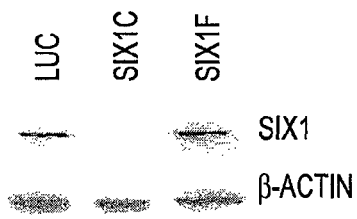
FIGS. 14-15 show that Six1 knockdown sensitizes OCC to TRAIL-mediated apoptosis. SKOV3 cells were transiently transfected with plasmids expressing siRNA sequences against Six1 and luciferase (Luc) as outlined in the methods.
Figure 15:
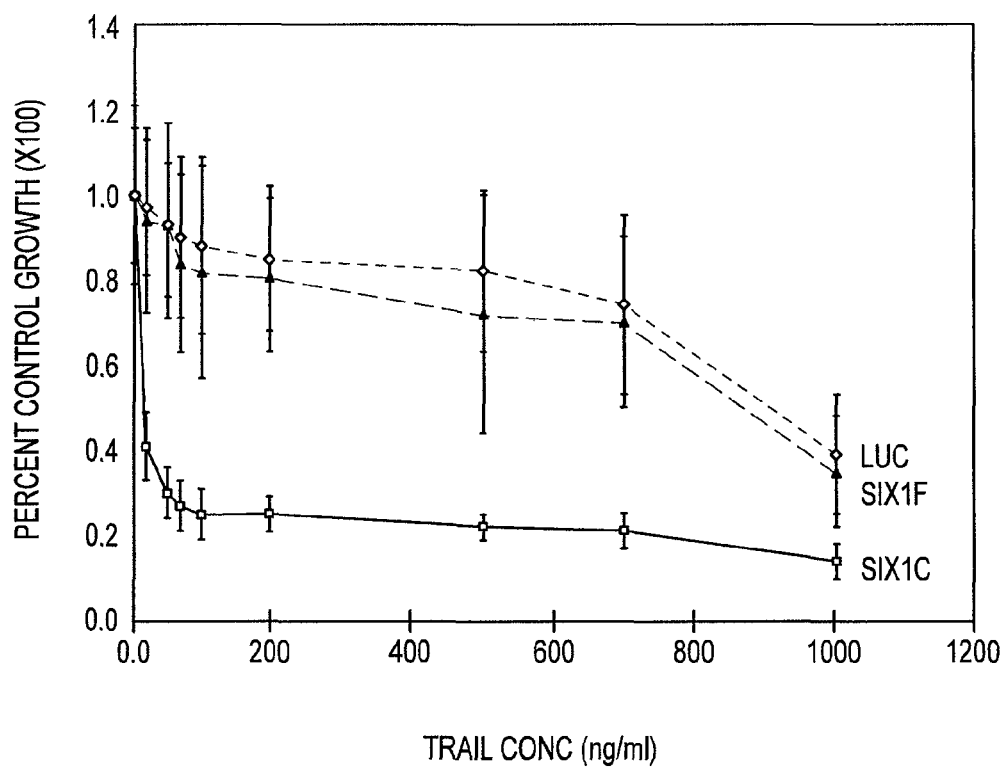
Figures 20, 21:
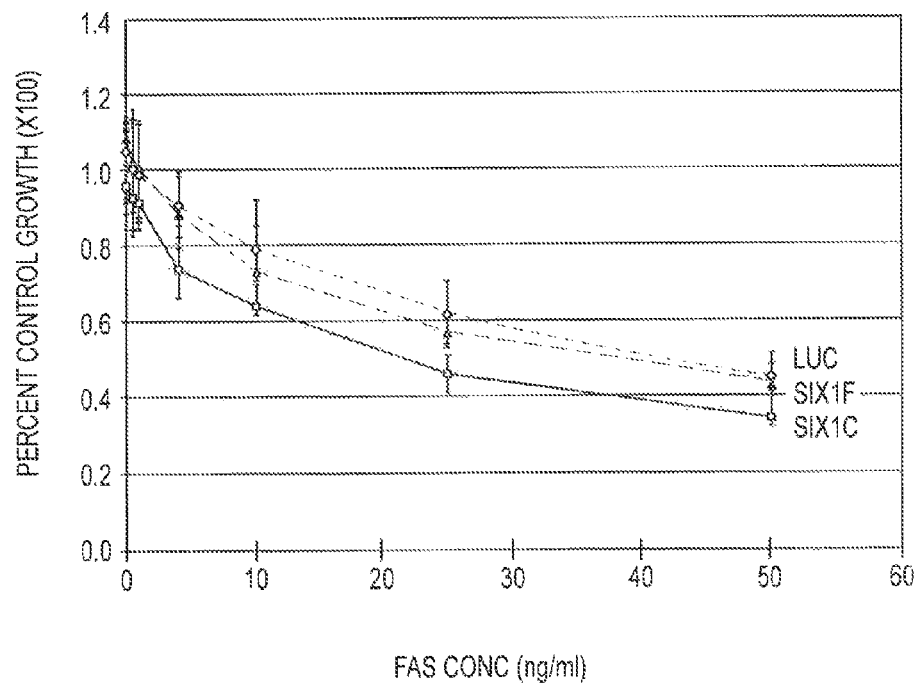
FIG. 20 shows the effect on FasL of Six1 knockdown in SKOV3.
FIG. 21 is a table listing Six1 specific primers and taqman probes used for analysis.

Six1 was knocked down in SKOV3 cells using targeted siRNA to determine whether high levels of Six1 in SKOV3 cells are responsible for resistance to TRAIL-mediated apoptosis. Two pSUPER-based siRNA constructs targeting Six1 were transfected into SKOV3 cells (Six1 C and Six1 F). In addition, a pSUPER construct targeting luciferase (Luc), which engages the siRNA machinery but does not affect Six1 levels, was transfected into SKOV3 cells as control. See FIG. 19 for mRNA sequences targeted by pSUPER sRNA vectors. When examined after completion of the TRAIL assay (5 days post-transfection), Six1 protein was almost completely absent in SKOV3 cells transfected with the pSUPER Six1C construct; however, the pSUPER Six1 F construct, while targeted to Six1, was ineffective, providing a second control for the effects of Six1 expression (FIG. 14). The pSUPER Luc siRNA had no effect on Six1 levels (FIG. 14). SKOV3 cells transfected with pSUPER Six1 C, in which Six1 was effectively knocked down, were almost 100 times more sensitive to TRAIL ($IC_{50}$~9 ng/ml TRAIL) compared to SKOV3 cells transfected with pSUPER Six1 F, which did not knock down Six1, or with the pSUPER luc control ($IC_{50}$s for both Six1 F and luc ~900 ng/ml TRAIL) (FIG. 15). In contrast, Six1 knockdown in SKOV3 cells resulted in only a modest (less than 2-fold) sensitization to FasL (FIG. 20). These results demonstrate that Six1 specifically and significantly inhibits TRAIL-mediated apoptosis.

Figure 16:
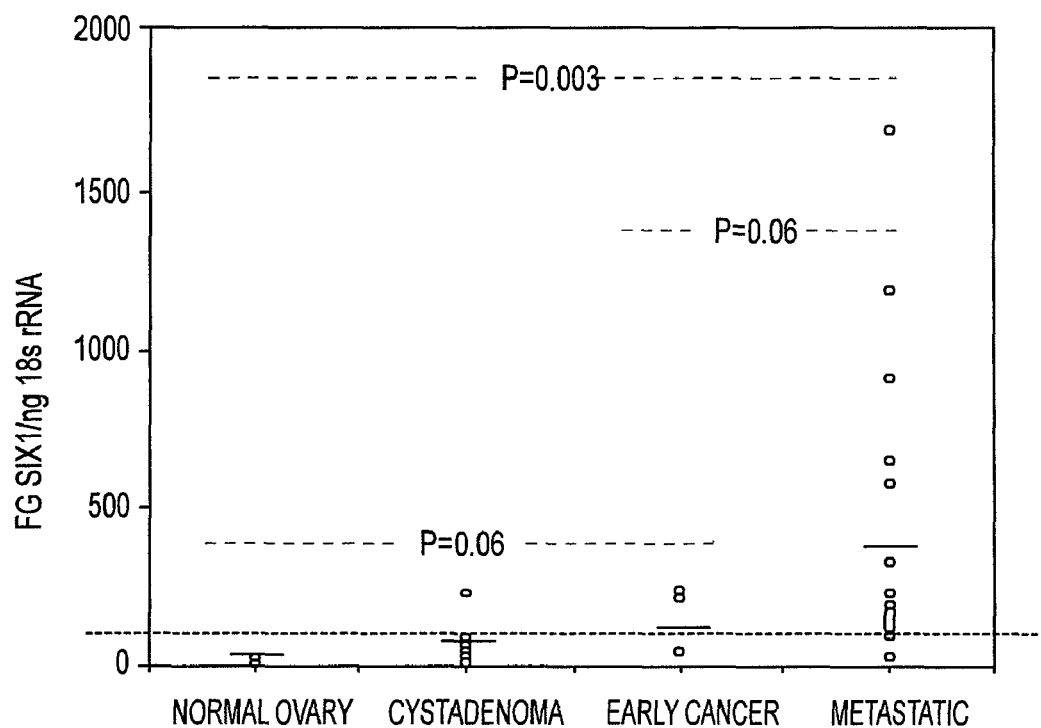
FIGS. 16-17 show that Six1 mRNA is overexpressed in ovarian carcinomas compared to normal ovary and is associated with poor prognosis in late stage cancers.

Six1 is over-expressed in ovarian carcinomas. The discovery that Six1 modulates the response of ovarian cancer cells to TRAIL has significant implications both for ovarian cancer prognosis as well, as for therapeutic interventions. To determine whether Six1 overexpression is prevalent in ovarian carcinomas, and whether its expression is related to cancer survival, RNA was isolated from normal ovaries, cystadenomas, and early (stage I) and late (stages II, III, and IV, all metastatic either locally or distant) stage ovarian carcinomas and qRT-PCR was performed to examine Six1 mRNA levels. Using a cut-off of 100 fg Six1/ng rRNA, 0/5 (0%) normal postmenopausal ovaries, 1/7 (14%) cystadenomas, 3/5 (60%) early stage cancers (stage I), and 13/19 (68%) metastatic cancers (stages I-IV) were shown to overexpress Six1 (FIG. 16). Six1 mRNA is elevated in early stage ovarian tumors compared to normal ovary (mean relative expression 140±53 fg/ng rRNA vs. 14±12 fg/ng rRNA, p=0.06) and in metastatic tumors compared to early stage tumors (mean relative expression 369±129 vs. 140±53, P=0.06). The numbers achieve statistical significance when metastatic tumors are compared to normal ovaries (p=0.003). These data demonstrate that Six1 mRNA is overexpressed in ovarian carcinoma, and suggest that Six1 expression contributes to a more malignant phenotype.

Figure 22:
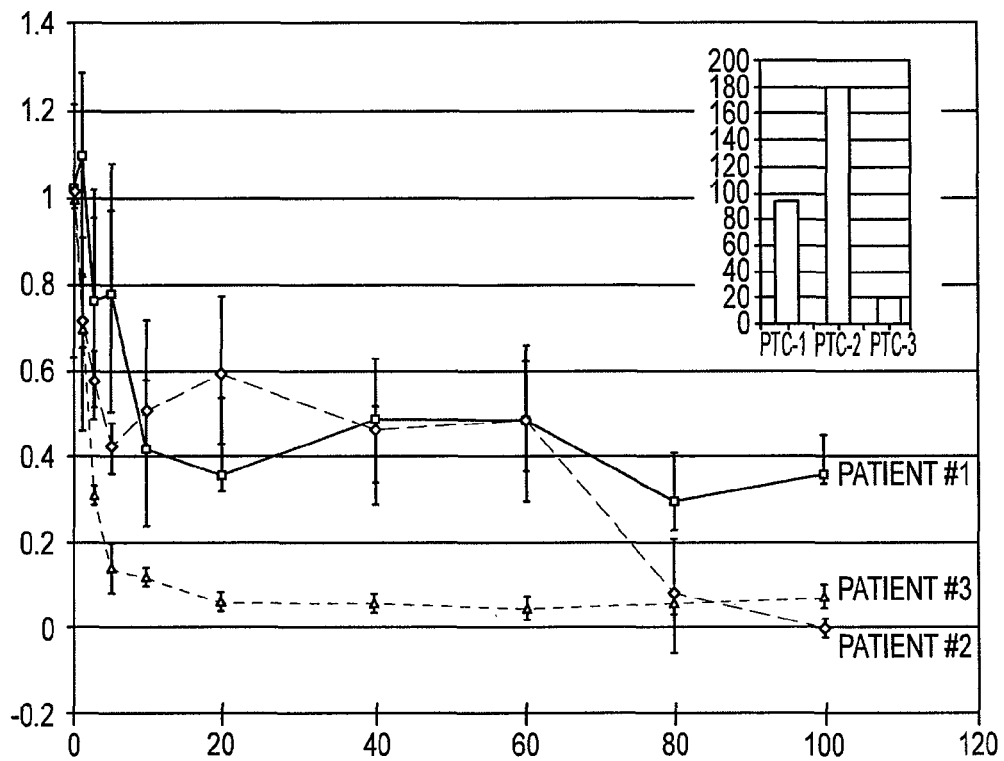
FIG. 22 shows patient patient-derived ovarian tumor cells with different levels of Six1 expression and their differences in TRAIL sensitivity.

Additional experiments to establish feasibility. Three patient patient-derived cell lines were examined and tested to see if differences in Six1 mRNA levels correlate with response to TRAIL. Primary patient tumor cells were isolated and maintained in culture. Six1 mRNA levels were measured by quantitative RT RT-PCR showing variable expression levels then treated with increasing concentrations of TRAIL and assayed for apoptosis. Tow lines (patient numbers 1 and 2) expressed high levels of Six1 by qRT qRT-PCR and one (patient number 3) expressed lower levels. (See FIG. 22). The low Six1 mRNA expressing cells from patient number 3 were markedly more sensitive to TRAIL in the dose dose-response assay.

Figure 23:
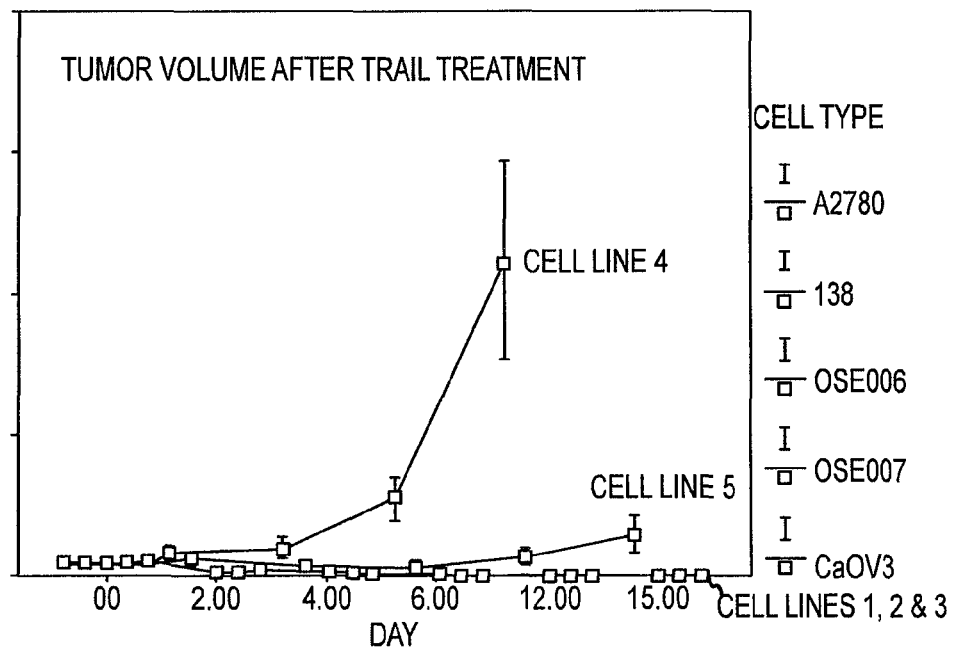
FIG. 23 shows that TRAIL treatment fails to cause tumor regression in vivo in tumor cells that have high Six 1.

In another experiment, tumors were established with different cell lines and then animals were treated for five days starting on day 0. Three low Six1 cell lines (cell lines 1, 2 and 3) demonstrated tumor regression while two high Six1 cell lines (cell lines 4 and 5) showed no regression in response to TRAIL treatment and continued to grow. (See FIG. 23). Accordingly, primary tumor cell lines can be worked with to test their sensitivity to TRAIL and other agonists and to test if Six1 mRNA and protein levels correlate with the functional effects on TRAIL receptor signaling.

Figure 17:
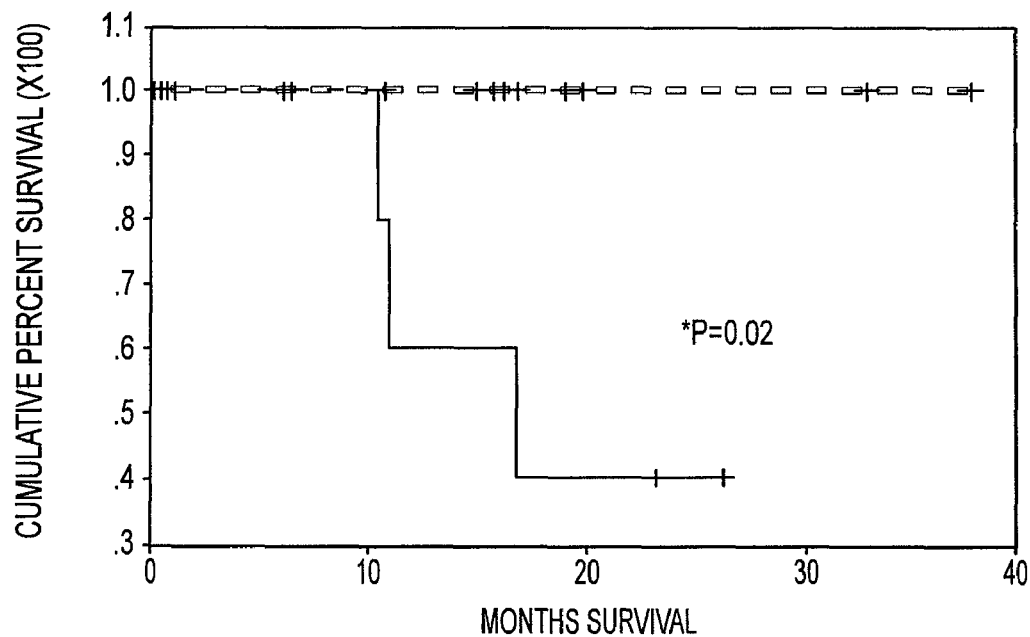

The relationship between levels of Six1 mRNA in patients with metastatic ovarian cancer and survival was determined to examine whether Six1 overexpression may contribute to a more malignant phenotype. In support of a role for Six1 in tumor progression, metastatic ovarian cancer patients expressing high levels of Six1 (greater than 300 fg/ng 18 s rRNA) exhibited significantly shortened survival at an overall median follow-up of 17 months than metastastic ovarian cancer patients with lower levels of Six1 overexpression. Of 6 ovarian cancer patients with Six1>300 fg/ng rRNA, four died with a median survival of 17 months, one is alive with disease and one is disease free at 19 months of follow-up. In contrast, the 13 ovarian cancer patients with late stage disease that exhibited Six1 levels below 300 fg/ng rRNA, are all alive with a median follow-up of 16 months and 9/13 are disease free. Survival effects observed are independent of stage, histology, extent of debulking or chemo-sensitivity. Thus, high levels of Six1 overexpression are significantly associated with poor clinical outcome (p=0.02) (FIG. 17).

The foregoing description is of exemplary embodiments of the subject invention. It will be appreciated that the foregoing description is not intended to be limiting; rather, the exemplary embodiments set forth herein merely set forth some exemplary applications of the subject invention. It will be appreciated that various changes, deletions, and additions may be made to the components and steps discussed herein without departing from the scope of the invention as set forth in the appended claims.

The invention claimed is:

1. A method for determining therapeutic intervention in a subject having ovarian cancer comprising the steps of:
   obtaining a biological sample from the subject;
   determining whether the biological sample possesses an overexpression of at least one of Six1 protein or Six1 RNA; and
   selecting a tumor necrosis factor-related apoptosis-inducing ligand (TRAIL) agent for therapy when at least one of Six1 protein or Six1 RNA is not overexpressed.

2. The method of claim 1 wherein the biological sample is a tumor sample.

3. The method of claim 2 where the tumor sample is an ovarian tumor sample.

4. A method for determining therapeutic intervention for a subject having ovarian carcinoma comprising the steps of:
   obtaining an ovarian tumor sample from the subject;
   determining an amount of Six1 protein or Six1 mRNA expressed in the ovarian tumor sample;
   determining whether the amount of Six1 protein or Six1 mRNA is over-expressed in the ovarian minor sample compared to a control; and
   selecting a TRAIL agent for therapy when Six1 is not overexpressed.

5. A method for determining the prognosis of a subject with ovarian carcinoma comprising the steps of:
   obtaining an ovarian tumor sample from the subject;
   determining the amount of Six t protein or Six1 RNA expressed in the tumor sample; and
   forming a prognosis based on the amount of Six1 protein or Six 1 RNA.

6. The method of claim 5 wherein the step of forming a prognosis comprises the steps of:
   comparing the amount of Six1 protein or Six1 RNA expressed in the ovarian tumor sample to a control; and
   forming the prognosis based on the amount of Six1 protein or Six1 RNA expressed in the ovarian tumor sample as compared to the control.

7. The method of claim 5 wherein the step of forming the prognosis based on the amount of Six1 protein or Six1 mRNA expressed in the ovarian tumor sample comprises forming a prognosis of increased mortality when Six1 expression levels in the ovarian tumor are greater than 300 fg/ng rRNA.

8. A method for determining therapeutic intervention in a subject having ovarian cancer comprising the steps of:
   obtaining a biological sample from the subject;
   determining whether the biological sample possesses an overexpression of a Six1 protein or Six1 RNA; and
   selecting a non-tumor necrosis factor-related apoptosis-inducing ligand agent for therapy that is not cross-resistant to chemotherapy when the biological sample does possess the over-expression.

9. The method of claim 8 wherein the biological sample is a tumor sample.

10. The method of claim 9 where the tumor sample is an ovarian tumor sample.

11. A method for determining therapeutic intervention in a subject having ovarian carcinoma comprising the steps of:
    obtaining an ovarian tumor sample from the subject;
    determining whether an amount of Six1 protein or Six] mRNA is over-expressed in the ovarian minor sample; and
    selecting a therapy that does not include tumor necrosis factor-related apoptosis-inducing ligand (TRAIL) when Six1 protein or Six1 mRNA is over-expressed.

* * * * *

UNITED STATES PATENT AND TRADEMARK OFFICE
CERTIFICATE OF CORRECTION

PATENT NO. : 8,283,119 B2
APPLICATION NO. : 12/518315
DATED : October 9, 2012
INVENTOR(S) : Heide Ford, Kian Behbakht and Andrew Thorburn It is certified that error appears in the above-identified patent and that said Letters Patent is hereby corrected as shown below:

In Column 15, line 22, please delete "minor" and insert therefor --tumor--.
In Column 15, line 29, please delete "Six t" and insert therefor --Six1--.
In Column 16, line 27, please delete "Six]" and insert therefor --Six1--.
In Column 16, line 28, please delete "minor" and insert therefor --tumor--.

Signed and Sealed this
Fourth Day of December, 2012

David J. Kappos
*Director of the United States Patent and Trademark Office*

SEQUENCE LISTING

<160> NUMBER OF SEQ ID NOS: 8

<210> SEQ ID NO 1
<211> LENGTH: 1378
<212> TYPE: DNA
<213> ORGANISM: Homo sapiens

<400> SEQUENCE: 1

```
ggtagcagca tccaccgggc gggaggtcgg aggcagcaag gccttaaagg ctactgagtg      60
cgccggccgt tccgtgtcca gaacctcccc tactcctccg ccttctcttc cttggccgcc     120
caccgccaag ttccgactcc ggttttcgcc tttgcaaagc ctaaggagga ggttaggaac     180
agccgcgccc ccctccctgc ggccgccgcc ccctgcctct cggctctgct ccctgccgcg     240
tgcgcctggg ccgtgcgccc cggcaggcgc cagccatgtc gatgctgccg tcgtttggct     300
ttacgcagga gcaagtggcg tcgtgtgcg aggttctgca gcaaggcgga aacctggagc     360
gcctgggcag gttcctgtgg tcactgcccg cctgcgacca cctgcacaag aacgagagcg     420
tactcaaggc caaggcggtg gtcgccttcc accgcggcaa cttccgtgag ctctacaaga     480
tcctggagag ccaccagttc tcgcctcaca accacccaa actgcagcaa ctgtggctga     540
aggcgcatta cgtggaggcc gagaagctgc gcggccgacc cctgggcgcc gtgggcaaat     600
atcgggtgcg ccgaaaattt ccactgccgc gcaccatctg ggacggcgag gagaccagct     660
actgcttcaa ggagaagtcg aggggtgtcc tgcgggagtg gtacgcgcac aatccctacc     720
catcgccgcg tgaagcggc gagctggccg aggccaccgg cctcaccacc acccaggtca     780
gcaactggtt taagaaccgg aggcaaagag accggccgc ggaggccaag gaaagggaga     840
```

```
acaccgaaaa caataactcc tcctccaaca agcagaacca actctctcct ctggaagggg    900
gcaagccgct catgtccagc tcagaagagg aattctcacc tccccaaagt ccagaccaga    960
actcggtcct tctgctgcag ggcaatatgg gccacgccag gagctcaaac tattctctcc   1020
cgggcttaac agcctcgcag cccagtcacg gcctgcagac ccaccagcat cagctccaag   1080
actctctgct cggccccctc acctccagtc tggtggactt ggggtcctaa gtggggaggg   1140
actgggccct cgaagggatt cctggagcag caaccactgc agcgactagg gacacttgta   1200
aatagaaatc aggaacattt ttgcagcttg tttctggagt tgtttgcgca taaggaatg    1260
gtggactttc acaaatatct ttttaaaaat caaaaccaac agcgatctca agcttaatct   1320
cctcttctct ccaactcttt ccacttttgc attttccttc ccaatgcaga gatcaggg    1378
```

<210> SEQ ID NO 2
<211> LENGTH: 284
<212> TYPE: PRT
<213> ORGANISM: Homo sapiens

<400> SEQUENCE: 2

```
Met Ser Met Leu Pro Ser Phe Gly Phe Thr Gln Glu Gln Val Ala Cys
  1               5                  10                  15

Val Cys Glu Val Leu Gln Gln Gly Gly Asn Leu Glu Arg Leu Gly Arg
                 20                  25                  30

Phe Leu Trp Ser Leu Pro Ala Cys Asp His Leu His Lys Asn Glu Ser
             35                  40                  45

Val Leu Lys Ala Lys Ala Val Val Ala Phe His Arg Gly Asn Phe Arg
         50                  55                  60

Glu Leu Tyr Lys Ile Leu Glu Ser His Gln Phe Ser Pro His Asn His
 65                  70                  75                  80

Pro Lys Leu Gln Gln Leu Trp Leu Lys Ala His Tyr Val Glu Ala Glu
                 85                  90                  95

Lys Leu Arg Gly Arg Pro Leu Gly Ala Val Gly Lys Tyr Arg Val Arg
            100                 105                 110

Arg Lys Phe Pro Leu Pro Arg Thr Ile Trp Asp Gly Glu Glu Thr Ser
        115                 120                 125

Tyr Cys Phe Lys Glu Lys Ser Arg Gly Val Leu Arg Glu Trp Tyr Ala
130                 135                 140

His Asn Pro Tyr Pro Ser Pro Arg Glu Lys Arg Glu Leu Ala Glu Ala
145                 150                 155                 160

Thr Gly Leu Thr Thr Thr Gln Val Ser Asn Trp Phe Lys Asn Arg Arg
                165                 170                 175

Gln Arg Asp Arg Ala Ala Glu Ala Lys Glu Arg Glu Asn Thr Glu Asn
            180                 185                 190

Asn Asn Ser Ser Ser Asn Lys Gln Asn Gln Leu Ser Pro Leu Glu Gly
        195                 200                 205

Gly Lys Pro Leu Met Ser Ser Glu Glu Glu Phe Ser Pro Pro Gln
    210                 215                 220

Ser Pro Asp Gln Asn Ser Val Leu Leu Leu Gln Gly Asn Met Gly His
225                 230                 235                 240

Ala Arg Ser Ser Asn Tyr Ser Leu Pro Gly Leu Thr Ala Ser Gln Pro
                245                 250                 255

Ser His Gly Leu Gln Thr His Gln His Gln Leu Gln Asp Ser Leu Leu
            260                 265                 270

Gly Pro Leu Thr Ser Ser Leu Val Asp Leu Gly Ser
        275                 280
```

```
<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gaacgagagc guacucaag                                                  19

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
aguccagacc agaacucgg                                                  19

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
cguacgcgga auacuucga                                                  19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cacctcccca aagtccagac                                                 20

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cctggcgtgg cccata                                                     16

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
cggtccttct gctgcagggc at                                              22
```